(12) United States Patent
Aechtner et al.

(10) Patent No.: US 7,294,392 B2
(45) Date of Patent: Nov. 13, 2007

(54) COMPOSITE MATERIAL AND METHOD FOR THE PRODUCTION THEREOF

(75) Inventors: Stefan Aechtner, Bad Säckingen (DE); Helga Hornberger, Nürnberg (DE); Emil Nagel, Bad Säckingen (DE); Norbert Thiel, Bad Säckingen (DE)

(73) Assignee: Vita Zahnfabrik H. Rauter GmbH & Co. KG, Bad Sackingen (DE)

( * ) Notice: Subject to any disclaimer, the term of this patent is extended or adjusted under 35 U.S.C. 154(b) by 0 days.

(21) Appl. No.: 10/469,548

(22) PCT Filed: Mar. 8, 2002

(86) PCT No.: PCT/EP02/02567

§ 371 (c)(1), (2), (4) Date: Oct. 29, 2003

(87) PCT Pub. No.: WO02/076907

PCT Pub. Date: Oct. 3, 2002

(65) Prior Publication Data

US 2004/0081847 A1    Apr. 29, 2004

(30) Foreign Application Priority Data

Mar. 10, 2001  (EP) .................................. 01105991

(51) Int. Cl.
- *B32B 3/26* (2006.01)
- *B32B 5/28* (2006.01)
- *B32B 5/30* (2006.01)
- *B32B 33/00* (2006.01)

(52) U.S. Cl. ................... 428/304.4; 428/210; 428/220; 428/306.6; 428/308.4; 428/325

(58) Field of Classification Search ................ 428/210, 428/325, 446, 688, 702, 304.4, 306.3, 308.4, 428/312.2, 312.6, 315.5, 306.6, 220

See application file for complete search history.

(56) References Cited

U.S. PATENT DOCUMENTS

| | | | | |
|---|---|---|---|---|
| 5,843,348 A | * | 12/1998 | Giordano | ..................... 264/19 |
| 5,869,548 A | * | 2/1999 | Ikushima et al. | ........... 523/116 |
| 6,159,417 A | | 12/2000 | Giordano | |

FOREIGN PATENT DOCUMENTS

| | | | |
|---|---|---|---|
| EP | 0 701 808 A2 | | 3/1996 |
| EP | 0 803 241 A2 | | 10/1997 |
| EP | 1 006 095 A2 | | 6/2000 |
| WO | WO01/10794 | * | 2/2001 |

* cited by examiner

*Primary Examiner*—Michael E. Lavilla
(74) *Attorney, Agent, or Firm*—Jacobson Holman PLLC

(57) ABSTRACT

A composite material with a porous inorganic-nonmetallic matrix and a second material, is characterized in that the porous inorganic-nonmetallic matrix has a bending strength of $\geq 40$ MPa as measured according to ISO 6 872; the second material is an organic material which at least partly fills the pores of the porous matrix; and the composite material has a modulus of elasticity, E, of $\geq 25$ GPa as measured according to ISO 10 477.

7 Claims, No Drawings

COMPOSITE MATERIAL AND METHOD FOR THE PRODUCTION THEREOF

This is a nationalization of PCT/EP02/02567 filed Mar. 8, 2002 and published in German.

The present invention relates to a composite material with a porous inorganic-nonmetallic network whose pores are filled with a polymer, a method for the preparation thereof, and applications of this composite material.

EP-A-1 006 095 relates to a method for the preparation of endodontic, orthodontic and direct restorations based on a ceramic network. A starting glass monomer is filled with a material to achieve improved flexibility and abrasion resistance. The infiltration material may be, for example, a glass which will form a layer having a hardness within a range of from 300 to 600 KHN and a modulus of elasticity within a range of from 70 to 80 GPa. Its bending strength is within a range of from 200 to 500 MPa. In the interior, the structure is to have a bending strength of about 150 to 80 MPa and a modulus of elasticity of from 15 to 25 GPa. The corresponding values are to be achieved by infiltration with a monomer and subsequent curing. Thus, a two-layered structure has been described which has different properties. Corresponding products have not been known to date.

EP-A-0 803 241 relates to a dental material made of a porous ceramic material which is filled into an artificial tooth, an inlay, an onlay, a crown, a crown bridge or within a block which is suitable for CAD/CAM processing. This material is sintered to form interconnected pores. This is followed by impregnation with an artificial resin. A drawback of these described products is the inaccurate definition and description of the supporting network. In many embodiments, this leads to a deterioration of the physical-technical data in comparison to composite materials common today. U.S. Pat. No. 5,843,348 relates to a method for the preparation of a ceramic network material from a ceramic suspension. This method involves the casting of a suspension into a mold which has a tooth-shaped design. The suspension contains dispersed aluminum oxide particles in a medium which contains deionized water with a pH within a range of from 4 to 5 and polyvinyl alcohol in a concentration of from 0.5 to 1% by weight. After drying, the suspension is fired in an oven at a temperature within a range of from 1000 to 1400° C. to produce a ceramic network. The porous structure is infused with lanthanum aluminosilicate glass to form a glass layer having a thickness within a range of from 1 to 2 mm within the ceramic network.

In Ullmann's Encyclopedia of Industrial Chemistry, different methods are described for the preservation of porous rock structures. Thus, the objects, for example, sculptures of sandstone or marble, are impregnated with hydrophobic reagents, such as alkyltrialkoxysilanes, and/or coupling agents, such as tetraethyl orthosilicate. For the stabilization of the structure, the pores are additionally infiltrated with monomers, for example, methyl methacrylate, under vacuum. After thermal curing under pressure, the objects are mechanically more stable, and more importantly, chemical decay is substantially prevented by closing the pores.

It is the object of the invention to provide a composite material which has a homogeneous poreless structure and properties which are between those of ceramic and conventionally filled polymer materials, and to provide a method for the preparation of such composite material.

This object is achieved by a composite material with a porous inorganic-nonmetallic matrix and a second material, characterized in that said porous inorganic-nonmetallic matrix has a bending strength of $\geq 40$ MPa as measured according to ISO 6 872;

said second material is an organic material which at least partly fills the pores of said porous matrix; and said composite material has a modulus of elasticity, E, of $\geq 25$ GPa as measured according to ISO 10 477.

The composite material according to the invention is advantageous because a new class of materials is obtained whose properties are between those of ceramic and plastic materials. For example, this class of materials is characterized, on the one hand, by a lower brittleness as compared to ceramic materials and, on the other hand, by an increased abrasion resistance as compared to the previous inorganic-filled polymers.

The inorganic-nonmetallic phase of the composite material according to the invention forms a network which has an intrinsic strength (bending strength of the porous inorganic-nonmetallic network prior to infiltration), $\sigma$, of $\geq 40$ MPa. This results in an increase of the modulus of elasticity of the composite material as compared to conventionally filled composites.

The composite material according to the invention preferably has a bending strength, $\sigma$, of $\geq 100$ MPa as measured according to ISO 6 872.

The pores of the porous network occupy a volume of from 5 to 85% by volume, preferably from 10 to 50% by volume, especially from 15 to 35% by volume. An advantage of the controllable porosity of the inorganic-nonmetallic network is the fact that the polymer content in the later composite material correlates therewith. An increase of the polymer content is related with an increase of the impact strength and a decrease of the specific gravity of the composite material.

Typically, the pores of the inorganic-nonmetallic network of the composite material according to the invention have a pore size of from 0.2 to 25 µm, preferably from 0.5 to 10 µm. The pore sizes and shapes to be employed are dependent on the combination of inorganic and polymer materials, on the contact angle between the inorganic material and the monomer or polymer, on the pretreatment and on the infiltration method employed.

The porous inorganic-nonmetallic network as an intermediate stage of the composite material according to the invention can be obtained, for example, by the sintering of powdery inorganic, especially ceramic, substances or mixtures of substances, the sintering process being completed, in particular, prior to the formation of closed pores. Further, it is preferred that the sintering process is discontinued only after the phase of necking or glass flow, which is typically associated with a sudden change of the intrinsic strength of the inorganic-nonmetallic network.

Preferably, the powdery inorganic substances or mixtures of substances employed have grain sizes which exhibit a bimodal distribution, e.g., fine and coarse grain sizes. The small grains have a higher sintering activity while the large grains determine the pore shape.

In a preferred embodiment, the inorganic-nonmetallic network of the composite material according to the invention comprises powdery inorganic substances or mixtures of substances which have a grain size of from 0.2 µm to 25 µm. Typical $d_{50}$ values (laser granulometry) of the starting materials employed are between 0.5 and 5 µm.

The inorganic-nonmetallic network of the composite material according to the invention is preferably constituted of at least two different powder mixtures having different sintering temperatures. The sintering activity is determined by the lower-melting powder components.

The pores of the inorganic-nonmetallic network advantageously have surfaces which possess hydrophobic properties. The hydrophobic properties can be achieved, for example, by superficial silanization. The hydrophobic surfaces increase the wettability by monomers of the porous network.

The silanization is effected simply by means of a silanizing agent in a liquid phase.

For the silanization of the porous inorganic-nonmetallic network, an alkoxysilane or halosilane, preferably 3-methacryloxypropyltrimethoxysilane, is employed.

In particular, the inorganic phase of the composite material according to the invention is an organic polymer which is formed in situ within the pores of the porous network by the polymerization of prepolymers, oligomers or monomers.

The organic polymer is formed from thermally polymerizable monomers and/or by chemically induced initiation reactions of polymerizable monomers and/or by condensable monomers.

The composite material according to the invention is preferably isotropic. This eliminates the disadvantages of today's anisotropic composites which have, for example, only low strengths when stressed against the preferential direction. Nevertheless, it can be imagined that some well-aimed anisotropy may be introduced into the composite material according to the invention. This can be effected, for example, by introducing fibers which are selectively cross-linked in other directions of space. Further, it is possible to prepare continuous gradient materials by using gradient ovens in the preparation of the inorganic-nonmetallic network.

The composite material according to the invention may contain auxiliary agents, such as antioxidants and pigments which are appropriate to the respective intended application.

The composite material according to the invention can be prepared, for example, by a method as follows:
preparing the inorganic-nonmetallic starting material;
shaping the inorganic-nonmetallic phase, either wet, for example, by a slip process, or dry, for example, by isostatic compression, optionally using a suitable binder system;
sintering the inorganic-nonmetallic network to the desired degree of sintering and porosity;
the sintering process being discontinued before substantially closed pores are formed in the sintered product;
and after the phase of necking and/or glass flow has been reached;
the porous product of inorganic-nonmetallic material obtained is first coated with a wetting agent, preferably silanes having a suitable functional group;
the inorganic-nonmetallic network is then completely infiltrated with monomers;
and subsequently polymerized with a suitable method, such as hot polymerization or microwaves.

In the method according to the invention, oxide ceramics, glasses, porcelains, non-oxide ceramics and combinations thereof, for example, are employed as the inorganic material.

In the method according to the invention, powdery inorganic materials having a grain size of from 0.2 µm to 25 µm, preferably from 0.5 to 10 µm ($d_{50}$ values as determined by laser granulometry), are employed, in particular.

Preferably, according to the invention, the inorganic material in a liquid form is infiltrated into the sintered inorganic material.

The wetting agent is preferably in solution. An advantage of the dilution is the decreased viscosity.

The wetting agent must contain a functional group capable of coupling.

According to the invention, organic monomers or prepolymers are introduced into the sintered inorganic-nonmetallic network and polymerized within the pores of the network to form the organic material.

According to the invention, the organic material can be introduced into the sintered inorganic material by pressure infiltration. The advantage thereof is the quickly achieved complete and homogeneous infiltration. Depending on the objective, it may be found advantageous to perform the polymerization under pressure.

Optionally, both the inorganic-nonmetallic network and the organic monomer may be evacuated prior to infiltration.

As the monomers, organic compounds are preferably employed which have at least one ethylenically unsaturated moiety, at least one condensable moiety or at least one moiety capable of ring-opening polymerization, or combinations thereof.

Suitable initiator systems for the polymerization are known and can be seen from the relevant literature.

For the preparation of translucent materials suitable for dental purposes, according to the invention, feldspar-containing powders and frits are employed as the inorganic material, and bismethacrylates are employed as the organic compound, and peroxide-containing compounds are employed as initiators.

The invention also relates to a compound material for dental applications which can be obtained by the method according to the invention.

The compound material according to the invention can be preferably employed for dental purposes, such as for inlays, onlays, crowns and bridges.

Compound materials prepared according to the invention can be used, inter alia, for the surface coating of ceramic and metallic materials, composites and plastic materials, as component parts having novel properties, such as modulus of elasticity, abrasion properties, specific gravity, heat distortion resistance. Further embodiments are sound-insulating and heat-insulating elements, friction bearings, members for vibration damping, electric isolators etc.

In particular, the composite material according to the invention can be employed as a friction bearing, for heat and/or sound insulation, or as a vibration damper.

The porous inorganic nonmetallic matrix having a bending strength of $\geq 40$ MPa as measured according to ISO 6 872 which can be employed for the preparation of the composite material according to the invention may serve as an intermediate product, and the invention also relates to such intermediate.

Preferably, the porous inorganic nonmetallic matrix according to the invention is formed from oxide ceramics, glasses, porcelains, non-oxide ceramics or combinations thereof.

In particular, the pores of the porous inorganic nonmetallic matrix according to the invention occupy a volume of from 5% by volume to 85% by volume, preferably from 10 to 50% by volume, especially from 15 to 35% by volume.

Also claimed according to the invention is a method for the preparation of a porous inorganic-nonmetallic matrix according to the invention;
wherein an inorganic nonmetallic material is mixed with a removable binder to form a moldable material;
the binder is removed to obtain a porous inorganic nonmetallic structure;
the porous inorganic nonmetallic structure is sintered;
to form said porous inorganic nonmetallic matrix.

The invention also relates to a method for the preparation of impressions from objects using the porous inorganic-nonmetallic matrix according to the invention. This method according to the invention is characterized in that:

an inorganic-nonmetallic material is mixed with a removable binder to form a moldable material;

said moldable material is contacted with an object from which an impression is to be prepared so that an impression of the object in the form of a negative is formed in the moldable material;

the moldable material is detached to obtain the shape of the object from which the impression is to be prepared, followed by removing the binder;

optionally followed by sintering and infiltrating the structure obtained after the removal of the binder.

In a further embodiment of the method mentioned, a method for the replication of objects is obtained. In this method, the method according to the invention for the preparation of impressions from objects is first performed. The matrix obtained thereby is itself subjected to the preparation of an impression to obtain a replicate of the object to be replicated. However, the method may also start from an impression of an object obtained in some other way to obtain a negative form from which an impression is then prepared according to the impression method according to the invention and optionally solidified.

Also claimed according to the invention is a mixture of powdery inorganic nonmetallic substances or mixtures of substances and a removable binder. This mixture is characterized in that said powdery inorganic nonmetallic substances or mixtures of substances have a grain size, $d_{50}$, of from 0.2 μm to 25 μm, and the binder is present in an amount of from 2% by weight to 50% by weight, based on the total weight of the mixture.

The powdery inorganic nonmetallic substances or mixtures of substances are preferably oxide ceramics, glasses, porcelains, non-oxide ceramics or combinations thereof.

Preferably, powdery inorganic substances or mixtures of substances with grain sizes having a bimodal distribution are employed.

In particular, the powdery inorganic nonmetallic substances or mixtures of substances for the preparation of the paste according to the invention have a grain size, $d_{50}$, of from 0.5 μm to 5 μm as measured by laser granulometry.

In the mixture according to the invention for the preparation of the paste, at least two different powders and/or mixtures of powders, having different sintering temperatures may be present. The paste according to the invention contains additives which allow a well-aimed curing according to the prior art.

The porous inorganic-nonmetallic matrix according to the invention can be used for obtaining molded parts which have advantageous properties; the invention also relates to such molded parts. The molded parts according to the invention can be prepared from porous sintered natural and/or synthetic feldspars or feldspatoids having a porosity which corresponds to a volume of from 5% by volume to 85% by volume, preferably from 10 to 50% by volume, especially from 15 to 35% by volume. By infiltration with suitable monomers and subsequent polymerization, transparent materials suitable for dental applications (e.g., use as inlays, onlays, veneers, crowns or bridges) can be prepared.

Particularly advantageous are multilayered molded parts having several layers with different properties in the layers, obtainable by coating different pastes with different resulting inorganic-nonmetallic matrix components, followed by sintering. The preparation of the complete composite material is then effected as previously described.

Molded parts having continuously changing properties can be prepared according to the invention, and the invention also relates to such molded parts. These molded parts can be obtained, for example, by sintering the inorganic-nonmetallic matrix in a gradient oven. Natural teeth are also anisotropic and comprised of several different layers. Typically, the molded parts according to the invention are prepared as follows:

preparing the work with the mouth, applying a release agent;

for cavities, direct preparation of an impression within the mouth using the paste according to the invention;

preliminary or final curing of the molded part, removing it from the cavity;

sintering to form pores with firing out the binder.

for crowns and bridges: preparing an impression from the preparation;

preparing the master;

building the restoration on the master using paste according to the invention;

sintering the work to form pores with firing out the binder.

The invention will be further illustrated using the following Examples.

EXAMPLE 1

A bimodal aluminum oxide having a $d_{50}$ of about 2.5 μm was pasted with distilled water and usual additives (in this case citric acid and Darvan) and ultrasonic treatment to form a suspension which is suitable as a slip. With this suspension, Delrin molds having dimensions of 1.2×4×20 mm were cast. After drying, the parts were taken from the mold and fired at a peak temperature of 1120° C. and a holding time of 2 hours.

The fired porous parts were then soaked with a 5% solution of methacryloxypropyltrimethoxysilane and again dried. Thereafter, the parts were evacuated and infiltrated over night at room temperature with an evacuated 1:1 mixture of urethane dimethacrylate and triethylene glycol dimethacrylate, followed by polymerization over a period of 17 hours, the peak temperature being 80° C.

On a Zwick universal testing machine, the parts exhibited an average bending strength of 300.15 MPa and a modulus of elasticity of 76.23 GPa.

EXAMPLE 2

A bimodal magnesium aluminum oxide spinel having a $d_{50}$ of about 2.5 μm was pasted with distilled water and usual additives (in this case citric acid and Darvan) and ultrasonic treatment to form a suspension which is suitable as a slip. With this suspension, Delrin molds having dimensions of 1.2×4×20 mm were cast. After drying, the parts were taken from the mold and fired at a peak temperature of 1180° C. and a holding time of 2 hours.

The fired porous parts were then soaked with a 5% solution of methacryloxypropyltrimethoxysilane and again dried. Thereafter, the parts were evacuated and infiltrated over night at room temperature with an evacuated 1:1 mixture of urethane dimethacrylate and triethylene glycol dimethacrylate, followed by polymerization over a period of 17 hours, the peak temperature being 80° C.

On a Zwick universal testing machine, the parts exhibited an average bending strength of 256.87 MPa and a modulus of elasticity of 82.89 GPa.

EXAMPLE 3

A bimodal mixture of 67% aluminum oxide and 33% zirconium dioxide having a $d_{50}$ of about 2.5 μm was pasted with distilled water and usual additives (in this case citric acid and Darvan) and ultrasonic treatment to form a suspension which is suitable as a slip. With this suspension, Delrin molds having dimensions of 1.2×4×20 mm were cast. After drying, the parts were taken from the mold and fired at a peak temperature of 1180° C. and a holding time of 2 hours.

The fired porous parts were then soaked with a 5% solution of methacryloxypropyltrimethoxysilane and again dried. Thereafter, the parts were evacuated and infiltrated over night at room temperature with an evacuated 1:1 mixture of urethane dimethacrylate and triethylene glycol dimethacrylate, followed by polymerization over a period of 17 hours, the peak temperature being 80° C.

On a Zwick universal testing machine, the parts exhibited an average bending strength of 287.42 MPa and a modulus of elasticity of 79.12 GPa.

EXAMPLE 4

A bimodal mixture of two feldspar frits (frit 1: firing temperature about 830° C., 10% proportion in the mixture; frit 2: firing temperature about 1180° C., 90% proportion in the mixture) having a $d_{50}$ of about 4.5 μm was pasted with a usual modeling liquid (water+binder additive) to form a suspension which is suitable as a slip. This suspension was shaken into metal molds having dimensions of 25×5×1.6 mm. After drying, the parts were taken from the mold and fired at a peak temperature of 940° C. and a holding time of about 40 minutes.

The fired porous parts were then soaked with a 5% solution of methacryloxypropyltrimethoxysilane and again dried. Thereafter, the parts were evacuated and infiltrated over night at room temperature with an evacuated 1:1 mixture of urethane dimethacrylate and triethylene glycol dimethacrylate, followed by polymerization over a period of 17 hours, the peak temperature being 80° C.

On a Zwick universal testing machine, the parts exhibited an average bending strength of 148.83 MPa and a modulus of elasticity of 30.04 GPa.

The parts exhibit an excellent translucency and are suitable for esthetic dental restorations due to their optical properties.

The invention claimed is:

1. An isotropic composite material comprising
   a porous inorganic-nonmetallic matrix having a bending strength greater than or equal to 40 MPa as measured according to ISO 6 872 and
   an organic material at least partly filling the pores of the porous inorganic-nonmetallic matrix,
such that the isotropic composite material has (i) a modulus of elasticity greater than or equal to 25 GPa as measured according to ISO 10 477 and (ii) a bending strength greater than or equal to 100 MPa as measured according to ISO 6 872.

2. The composite material according to claim 1, characterized in that the inorganic-nonmetallic matrix comprises a sintered powdery inorganic substance or mixture thereof, the powdery inorganic substance having a bimodal distribution grain size.

3. The composite material according to claim 2, characterized in that the grain size $d_{50}$ is 0.2-25 μm as measured by laser granulometry.

4. The composite material according to claim 2, characterized in that the grain size $d_{50}$ is 0.5-5 μm as measured by laser granulometry.

5. The composite material according to claim 1, characterized in that the inorganic-nonmetallic matrix comprises a sintered mixture of at least two powdery inorganic substances having different sintering temperatures.

6. The composite material according to claim 1, characterized in that the inorganic-nonmetallic matrix has pore surfaces coated with a coupling agent rendering the pore surfaces hydrophobized and provided with functional groups.

7. The composite material according to claim 1 further comprising silanized pore surfaces of the inorganic-nonmetallic matrix characterized in that the silanizing agent is aminopropyltriethoxysilane, vinyltriethoxysilane, 3-methacryloxypropyltrimethoxysilane, or a mixture thereof.

* * * * *